United States Patent [19]

Terao et al.

[11] Patent Number: 4,727,078
[45] Date of Patent: Feb. 23, 1988

[54] 7-PHENYL-7-(3-PYRIDYL)-6-HEPTENOIC ACID OR DERIVATIVES THEREOF WHICH INHIBIT THE ACTIVITY OF THROMBOXANES SYNTHETASE

[75] Inventors: Shinji Terao, Osaka; Kohei Nishikawa, Kyoto, both of Japan

[73] Assignee: Takeda Chemical Industries, Ltd., Osaka, Japan

[21] Appl. No.: 502,603

[22] Filed: Jun. 9, 1983

[30] Foreign Application Priority Data

Jun. 14, 1982 [JP] Japan .................................. 57-102488
Dec. 1, 1982 [JP] Japan .................................. 57-211753

[51] Int. Cl.$^4$ .................... C07D 213/55; A01N 31/44
[52] U.S. Cl. .................................. 514/277; 546/267; 546/269; 546/283; 546/342; 546/284
[58] Field of Search ............. 546/284, 267, 269, 283, 546/342; 424/263; 514/332, 336, 337, 342, 277

[56] References Cited

U.S. PATENT DOCUMENTS

4,518,602 5/1985 Terao et al. .................... 514/332

OTHER PUBLICATIONS

Terao et al., Chem. Abstracts, vol. 100, (19), Abst. 156,509s, May 7, 1984.
Terao et al., Chem. Abstracts, vol. 100, (210, Abst. 174,676y, May 21, 1984.
Terao et al., Chem. Abstracts, vol. 102, (11), Abst. 91,907q, Mar. 18, 1985.
J. Med. Chem. 24 1139 1981—Iizuka et al.—Highly Selective Inhibitors of Thromboxane Synthetase, 1. Imidazol Derivatives.
J. Med. Chem. 24 1149 1981—Iizuka et al.—Highly Selective Inhibitors of Thromboxane Synthetase, 2. Pyridine Derivatives.

*Primary Examiner*—Alan L. Rotman
*Attorney, Agent, or Firm*—Wegner & Bretschneider

[57] ABSTRACT

Novel compound of the formula:

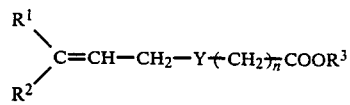

wherein $R^1$ is pyridyl group, $R^2$ is a phenyl group, a thienyl group, a furyl group, a naphthyl group, a benzothienyl group or pyridyl group, which may optionally have a lower alkoxy group, a lower alkyl group, a halogen atom, trifluoromethyl group, a lower alkenyl group or methylenedioxy group, $R^3$ is hydrogen atom or a lower alkyl group, and n is an integer of 0 to 6, Y is sulphur atom, methylene group or a group of the formula:

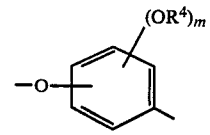

wherein $R^4$ is hydrogen atom or acetyl group, and m is 0 or 1, and their pharmaceutically acceptable salts have an inhibitory action on bio-synthesis of thromboxane $A_2(TXA_2)$ and an effect of accelerating the productivity of prostaglandin $I_2(PGI_2)$, and can be used for mammals to the prophylaxis or therapy of thrombosis caused by platelet aggregation or ischemic diseases caused by vasospasms in cardiac, cerebral and peripheral circulatory system (e.g. cardiac infarction, apoplexy, infarct of blood vessels in kidney, lung and other organs, pectic ulcer, etc.).

2 Claims, No Drawings

7-PHENYL-7-(3-PYRIDYL)-6-HEPTENOIC ACID OR DERIVATIVES THEREOF WHICH INHIBIT THE ACTIVITY OF THROMBOXANES SYNTHETASE

This invention relates to novel substituted vinyl carboxylic acid derivatives having an activity of specifically inhibiting the enzymic synthesis of thromboxane $A_2(TXA_2)$.

The present inventors have conducted analytical investigation, from the standpoint of molecular orbital theory, on factors of the three-dimensional structure of prostaglandin $H_2(PGH_2)$ which plays a role of the substrate for enzymic synthesis of thromboxane $A_2(TXA_2)$, studied the construction of molecular model having an inhibitory activity on the enzymic synthesis of thromboxane $A_2$, and found a group of pharmacologically excellent compounds having a novel structure and an inhibitory activity on the enzymic synthesis of thromboxane $A_2$, and thus the present invention has been completed.

More specifically, this invention relates to:
(1) Substituted vinyl carboxylic acid derivatives representable by the formula;

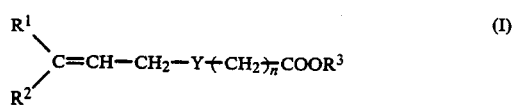 (I)

wherein $R^1$ stands for pyridyl group, $R^2$ stands for a phenyl group, a thienyl group, a furyl group, a naphthyl group, a benzothienyl group or a pyridyl group which may have a lower alkoxy group, a lower alkyl group, a halogen atom, trifluoromethyl group, a lower alkenyl group or methylenedioxy group, Y stands for a sulphur atom, methylene group or a group representable by the general formula;

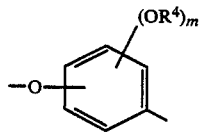

(where $R^4$ stands for hydrogen atom or acetyl group, and m denotes 0 or 1), $R^3$ stands for hydrogen atom or a lower alkyl group, and n denotes an integer of 0 to 6, and a pharmaceutically acceptable salt thereof.

In the above formula (I), the pyridyl group representable by $R^1$ or $R^2$ may be any one of 2-pyridyl, 3-pyridyl and 4-pyridyl, and, the thienyl, furyl, naphthyl and benzothienyl may respectively be any one of 2-thienyl and 3-thienyl; 2-furyl and 3-furyl; α-naphthyl and β-naphthyl; 2-benzothienyl, 3-benzothienyl, 4-benzothienyl, 5-benzothienyl, 6-benzothienyl and 7-benzothienyl.

As the substituents of phenyl, furyl, thienyl, naphthyl, benzothienyl and pyridyl shown by $R^2$, there may be mentioned a lower alkoxy group, a lower alkyl group, a halogen atom and a lower alkenyl group, which are respectively exemplified by groups having 1 to 4 carbon atoms such as methoxy, ethoxy, n-propoxy, i-propoxy, n-butoxy, i-butoxy, t-butoxy, etc.; groups having 1 to 5 carbon atoms such as methyl, ethyl, n-propyl, i-propyl, n-butyl, i-butyl, t-butyl, n-pentyl, i-pentyl, etc.; fluorine, chlorine, bromine, etc.; and groups having 2 to 5 carbon atoms such as vinyl, allyl, pentenyl, etc. When the phenyl, thienyl, furyl, naphthyl, benzothienyl or pyridyl shown by $R^2$ has a substituent, the substitution may take place at an optional position of the ring. As the lower alkyl shown by $R^3$ in the formulas (I), there may be mentioned groups having 1 to 4 carbon atoms such as methyl, ethyl, n-propyl, n-butyl, t-butyl, etc.

The compounds of the general formula (I) may be in a form of pharmaceutically acceptable salt or addition salt. The addition salts may be those with, for example, hydrochloric acid, hydrobromic acid, phosphoric acid, sulfuric acid, citric acid, succinic acid, maleic acid, fumaric acid, methanesulfonic acid or benzenesulfonic acid. When $R^3$ of the compound (I) is hydrogen, the compound (I) may be an alkali metal salt such as sodium salt or potassium salt, or an alkaline earth metal salt such as calcium salt.

Typical examples of the compound (I) may be enumerated as 7-phenyl-7-(3-pyridyl)-6-heptenoic acid, 8-phenyl-8-(3-pyridyl)-7-octenoic acid, 7-(2-thienyl)-7-(3-pyridyl)-6-heptenoic acid, 8-(2-thienyl)-8-(3-pyridyl)-7-octenoic acid or 7-(2-naphthyl)-7-(3-pyridyl)-6-heptenoic acid.

The substituted vinyl carboxylic acid derivatives of the formula (I) and the salts thereof have a strong inhibitory action on thromboxane-synthetase solubilized and fractionated from blood platelet microsome of men, cows or horses, and these compounds show a strong inhibitory action on bio-synthesis of thromboxane $A_2(TXA_2)$ in vivo.

The compounds (I) and salts thereof of this invention have also an increasing effect on the production of prostaglandin $I_2(PGI_2)$ showing a dilating action of arterial smooth muscle, an inhibitory action of platelet aggregation or an action of re-dissociation of platelet aggregation.

More specifically, prostaglandin $G_2(PGG_2)$ or prostaglandin $H_2(PGH_2)$ are important intermediates of thromboxane $A_2$, prostanglandin $I_2$ and other prostaglandins, and the compounds (I) and salts thereof of this invention show an inhibitory action on the enzyme capable of converting $PGH_2$ or $PGG_2$ into thromboxane $A_2$ (thromboxane $A_2$ synthetase) at an extremely low concentration (not higher than $3 \times 10^{-8}$ mol.), while showing no substantial action of inhibiting, for example, enzymes capable of converting $PGH_2$ or $PGG_2$ into prostaglandin $I_2$ and other prostaglandins which are physiologically required, for example, $PGI_2$ synthetase and other prostaglandin synthesizing enzymes, rather having beneficial effect in accelerating the efficiency of utilizing $PGG_2$ to cause the production of $PGI_2$ in the living body.

As explained above, substituted vinyl carboxylic acid derivatives representable by the formula (I) and salts thereof specifically inhibit the action of thromboxane $A_2(TXA_2)$ synthetase without exerting substantial influence upon the action of prostaglandin $I_2(PGI_2)$ synthetase or prostaglandin synthetase (fatty acid cycloxygenase).

The compounds (I) and salts thereof of this invention have remarkably less toxicity [For example, no mouse was dead for 14 days when 7-phenyl-7-(3-pyridyl)-6-heptenoic acid was orally administered in an amount of 1000 mg/kg to five mice], and there is characteristically a wide margin between the amount showing toxicity and that showing pharmacological effects. Therefore, the compounds of this invention are of less undersirable side-effect, and can be used for mammals (e.g. rabbits, guinea pigs, dogs, human beings, etc.) for the prophylaxis or therapy of thrombosis caused by platelet aggregation or ischemic diseases caused by vasospasms in cardiac, cerebral and peripheral circulatory system (e.g. cardiac infarction, angina pectoris stroke, ischemic disease in the kidney, lung and other organs, peptic ulcer, etc.).

For practical administration, the compound of this invention can be used orally as tablet, capsule, power or granule and non-orally as injection or pellet. The dosage for oral use normally ranges from 50 mg to 500 mg per adult per day, and from 50 mg to 200 mg for non-oral use, divided in 1-3 times a day.

Among the compounds of the formula (I), the compounds of the formula:

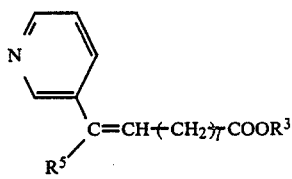
(I-1)

wherein $R^5$ is a phenyl group or a thienyl group, which may have a lower alkoxy group, a lower alkyl group, a halogen atom or trifluoromethyl group, l is an integer of 3 to 7, and $R^3$ has the meaning given above, and pharmaceutically acceptable salts thereof are preferable from the viewpoint of inhibitory action of thromboxane $A_2$ synthetase.

Alkoxy groups, lower alkyl groups and halogen atoms, which are the substituents of phenyl group or thienyl group, shown by $R^5$ are all of the same type as those of $R^2$, respectively. Thienyl group shown by $R^5$ is also the same as that shown by $R^2$.

The compound (I) can be prepared (1) by reacting a compound of the formula:

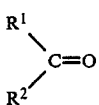
(II)

wherein $R^1$ and $R^2$ are of the same meaning as defined above, with a compound of the formula:

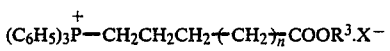
(III)

wherein $R^3$ and n are of the same meaning as defined above and X is a halogen atom, or (2) by reacting a compound of the formula:

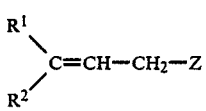
(IV)

wherein $R^1$ and $R^2$ are of the same meaning as defined above and Z is a halogen atom, with a compound of the formula:

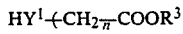
(V)

wherein $R^3$ and n are of the same meaning as defined above and $Y^1$ is sulfur atom or a group of the formula:

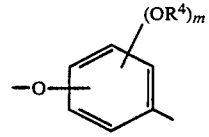

wherein $R^4$ and m are of the same meaning as defined above.

The reaction of the compound (II) with the compound (III) gives a compound of the formula:

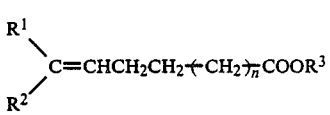
(Ia)

wherein each symbol is of the same meaning as defined above, and the reaction of the compound (IV) with the compound (V) gives a compound of the formula:

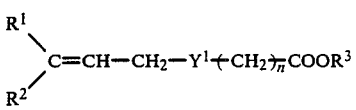
(Ib)

wherein each symbol is of the same meaning as defined above.

As the halogen atom shown by X in the formula (III) or shown by Z in the formula (IV), there may be mentioned chlorine or bromine, for example.

The reaction of the compound (II) with the compound (III) is usually conducted in the presence of a base in a solvent used. As such bases are enumerated, for example, n-butyl lithium, sodium hydride or potassium tertiary butoxide. Among them, n-butyl lithium and sodium hydride are preferably employed. The base is used usually in an amount of 1.5 to 4 moles, preferably in an amount of 2 to 3 moles, per mole of compound (III). As the solvent, there may be mentioned, for example, ether, tetrahydrofuran, dimethylformamide, dimethylsulfoxide or a mixed solvent of two or more of them. In this reaction, one mole of compound (II) is usually contacted with 0.8 to 1.2 mole of compound (III).

The reaction is conducted preferably under the atmosphere of a dry inert gas (e.g. nitrogen, argon and helium gases.) The reaction temperature ranges from $-10°$ C. to $50°$ C., preferably from $0°$ C. to $30°$ C. The progress of the reaction can be recognized by observing the disappearance of the specific color of the phospholane, and, in general, the reaction completes in about 1-6 hours.

The reaction between a compound representable by the general formula (IV) and a compound representable by the general formula (V) is usually conducted in a solvent in the presence of a base. As such bases are preferably mentioned, for example, sodium hydride, potassium tertiary butoxide, potassium carbonate or sodium methoxide. The base is used usually in an amount of 0.8 to 2 moles, preferably in an amount of 1 to 1.5 mole, per mole of compound (V). As the solvent, there may be enumerated, for example, ether, tetrahydrofuran, dimethylformamide, dimethylsulfoxide or a mixed solvent of two or more of them. In this reaction, one mole of compound (IV) is usually contacted with 0.8 to 1.2 mole of compound (V).

The reaction temperature ranges usually from $-10°$ C. to $60°$ C., preferably $0°$ C.–$30°$ C., and the reaction time ranges usually from 1 to 3 hours.

Thus prepared substituted vinyl carboxylic acid derivatives (I) can be separated and refined by a per se conventional method such as extraction, concentration, crystallization or liquid-chromatography.

The compounds (I) are in the category of tri-substituted olefinic compounds including, depending on the cases, two types of geometrical isomers. Separation of such isomers may be conducted by, for example, fractional crystallization or chromatography.

When a compound (I) takes the form of carboxylic acid [$R^3$ in the formula (I) is hydrogen], it can be led to an ester form [$R^3$ in the formula (I) is a lower alkyl] and conversely, when a compound (I) takes the form of an ester, it can be led to the form of a free carboxylic acid.

Each of compounds of the formula (I-1) has two geometrical isomers of the formulas:

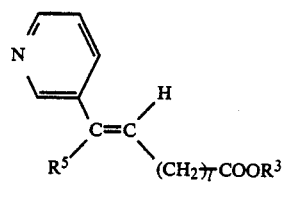

(I-1a)

and

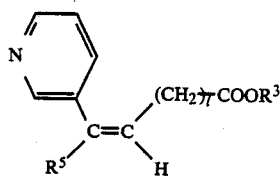

(I-1b)

wherein each symbol has the meaning given above.

In the following description of this invention, the compound wherein, as in the case of compounds represented by the formula (I-1a), the pyridine ring substituting one of the carbon atoms involved in the vinyl double bond and the hydrogen atom substituting the other carbon atom are disposed in the same direction will be referred to as the E isomer and the compound wherein, as in the case of compounds represented by formula (I-1b), the pyridine ring substituting one of the carbon atoms involved in the vinyl double bond and the hydrogen atom substituting the other carbon atom are disposed in the opposite direction will be referred to as the Z isomer.

The Z isomer (I-1b) can be isomerized to the E isomer (I-1a) by isomerization reaction which comprises heating the Z isomer in the presence of a mineral acid.

The isomerization reaction is generally conducted either in water or in an aqueous organic solvent. This aqueous organic solvent should basically be a solvent that will not be decomposed by mineral acids. Thus, for example, mixtures of water with acetic acid, formic acid, etc. may be mentioned. The mineral acid may for example be hydrochloric acid, sulfuric acid, phosphoric acid, hydrobromic acid, perchloric acid, methanesulfonic acid or the like, although hydrochloric acid, hydrobromic acid or phosphoric acid is preferably employed. This acid is generally used in the proportion of about 6 to 15 moles per mole of the starting compound (I-1b). The reaction temperature is generally about $50°$ to $140°$ C. and preferably about $100°$ to $130°$ C. At a lower temperature, the reaction is undesirably retarded. The reaction time varies with the kind and amount of the acid catalyst used and the heating temperature. Generally, such reaction conditions are selected as would reach an equilibrium of acid isomerization in about 10 to 40 hours.

This reaction is an equilibrium reaction between E isomer (I-1a) and Z isomer (I-1b), and by subjecting either the E isomer or the Z isomer or an optional mixture of E and Z isomers to the isomerization reaction, it can be converted to a mixture consisting of about 60 to 70% of E isomer (I-1a) and about 30 to 40% of Z isomer (I-1b). Since, as aforementioned, the E isomer is pharmacologically superior to the Z isomer, this reaction is advantageously applied to mixtures containing 40% or more of Z isomer.

When this reaction is conducted using a compound of general formula (I-1b) wherein $R^3$ is a lower alkyl group as a starting material, a hydrolysis reaction takes place concurrently to give the Compound (I-1a) wherein $R^3$ is hydrogen.

The product compound (I-1a) (E isomer) obtainable by this reaction can be isolated and purified by such procedures as, for example, adjusting the reaction mixture to pH 5.0 to 6.0 with aqueous ammonia, sodium hydroxide, potassium hydroxide or the like, extracting the product compound with an organic solvent such as ethyl acetate, chloroform, dichloromethane or the like and subjecting the extract to the conventional purification procedure such as crystallization or chromatography. The yield of this isomerization reaction can be improved by repetitive application thereof to the residual Z isomer-rich mixture remaining after isolation, for example by fractional crystallization, of E isomer (I-1a).

When the compounds of general formula (I-1a) and (I-1b) are carboxylic acids [In formulas (II) and (III), $R^3$ is a hydrogen atom], these acids can, if necessary, be esterified to the corresponding esters [In formulas (I-1a) and (I-1b), $R^2$ is a lower alkyl group]. Conversely, if the compounds (I-1a) and (I-1b) are esters, they can be hydrolyzed to the free carboxylic acids.

The compound (I-1) obtained in the reaction of compound (II) with compound (III) or in the reaction of compound (IV) with compound (V) is a substantially equimolar mixture of E and Z isomers. This mixture can be directly used in the practice of this invention but it is of course possible to separate the E and Z isomer from each other by way of fractional recrystallization or liquid chromatography and subjecting the Z isomer alone to the isomerization reaction mentioned above.

A compound (IV) can be prepared by allowing vinyl magnesium halide to react with a compound (II) to give a compound representable by the general formula:

(VI)

wherein each symbol is of the same meaning as defined above, followed by subjecting the compound (VI) to halogenization.

The reaction between a compound (II) and vinyl magnesium halide is conducted in, for example, ether, tetrahydrofuran or a mixture thereof under the atmosphere of an inert gas such as nitrogen or helium at a temperature ranging from −5° C. to room temperature.

Halogenation of a compound (VI) is conducted by allowing a halogenating agent such as thionyl chloride, thionyl bromide, phosphorus pentachloride, phosphorus trichloride or phosphorus tribromide, to react with a compound (VI) in a solvent such as methylene chloride, chloroform, ether or isopropyl ether. The compound (IV) thus prepared is unstable, and special attention should be paid to the reaction temperature. The reaction temperature ranges usually from about −20° C. to about 20° C. Thus-obtained halide (IV) can be used without purification for condensation with a compound (V).

A compound (II) can be prepared by, as shown by the following reaction schema, allowing an organic lithium compound to react with an aldehyde compound to give a compound (VII), which is then allowed to react with manganese dioxide or dimethylsulfoxide-oxalyl chloride.

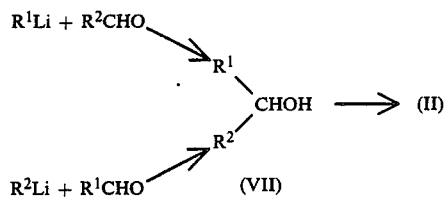

The following Reference Examples, Examples and Experimentals illustrate the present invention more concretely:

REFERENCE EXAMPLE 1

Process A

3-Brompyridine (10.0 g, 63 mmoles) was dissolved in ether (200 ml) under argon, which was cooled to −30° C. To this solution was added dropwise a n-butyl lithium hexane solution (1.62 mol. concentration, 40 ml) during 10 minutes, then the mixture was stirred for 5 minutes under the same reaction conditions. The reaction temperature was gradually raised to room temperature, then water (300 ml) was added to the reaction mixture, which was subjected to extraction with ethyl acetate (300 ml). The organic layer was washed with water, dried (magnesium sulfate) and concentrated under reduced pressure. The residue was subjected to a silica-gel chromatography using ethyl acetate to give the desired secondary alcohol compound (VIIa-2 in Table 1) (9 g, 76%)

Secondary alcohol compounds (VIIa-1–VIIa-22) prepared by a method analogous to the above-mentioned process are collectively listed in Table 1.

Process B

Benzothiophene (2.0 g, 14.9 mmoles) was dissolved in tetrahydrofuran (6 ml) and ether (12 ml) under argon. To the solution was added dropwise n-butyl lithium (1.62 molar concentration, 2.5 ml) in hexane at a temperature ranging from −20° C. to 0° C., whereupon the solution became blue. Fifteen minutes later, to the solution was added dropwise a solution of nicotinaldehyde (1.6 g) in tetrahydrofuran (5 ml) at a temperature ranging from 0° C. to 25° C. The mixture is stirred for one hour. To the reaction solution was added water (50 ml), and the mixture was subjected to extraction with ethyl acetate. The ethyl acetate layer was separated and purified by per se known method to give a secondary alcohol compound (VIIa-23 in Table 1) (2.1 g). Data including physico-chemical properties are shown in Table 1.

TABLE 1

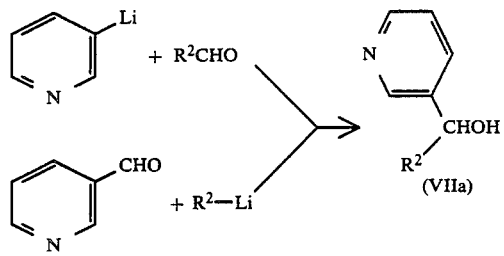

| Compound No. | R² | m.p. | Elemental Analysis Calc. | Found |
|---|---|---|---|---|
| VIIa-1 | ⟨4-MeO-C₆H₄-CH₂-⟩ | 106–107° C. | C 72.54<br>H 6.09<br>N 6.51 | 72.41<br>6.15<br>6.70 |
| VIIa-2 | ⟨4-iPr-C₆H₄-CH₂-⟩ | 107–108° C. | C 79.26<br>H 7.54<br>N 6.16 | 79.51<br>7.35<br>6.17 |

TABLE 1-continued $$\begin{array}{c}\text{3-Pyridyl-Li} + R^2\text{CHO} \\ \text{3-Pyridyl-CHO} + R^2\text{-Li}\end{array} \longrightarrow \begin{array}{c}\text{3-Pyridyl-CHOH-}R^2 \\ \text{(VIIa)}\end{array}$$

| Compound No. | $R^2$ | m.p. | Elemental Analysis | Calc. | Found |
|---|---|---|---|---|---|
| VIIa-3 | 4-Br-phenyl | 125–126° C. | C | 54.57 | 54.50 |
|  |  |  | H | 3.82 | 3.76 |
|  |  |  | N | 5.30 | 5.31 |
| VIIa-4 | 3-Br-phenyl | 95–96° C. | C | 54.57 | 54.53 |
|  |  |  | H | 3.82 | 3.86 |
|  |  |  | N | 5.30 | 5.32 |
| VIIa-5 | 2-Br-phenyl | 125–126° C. | C | 54.57 | 54.51 |
|  |  |  | H | 3.82 | 3.86 |
|  |  |  | N | 5.30 | 5.31 |
| VIIa-6 | 3-OMe-4-OPr-phenyl | 72–73° C. | C | 70.31 | 69.99 |
|  |  |  | H | 7.01 | 6.89 |
|  |  |  | N | 5.13 | 5.19 |
| VIIa-7 | 2-PrO-3-OMe-phenyl | 79–80° C. | C | 70.31 | 70.44 |
|  |  |  | H | 7.01 | 6.96 |
|  |  |  | N | 5.13 | 5.39 |
| VIIa-8 | 3,4-methylenedioxyphenyl | 105–106° C. | C | 68.11 | 68.07 |
|  |  |  | H | 4.84 | 4.57 |
|  |  |  | N | 6.11 | 6.14 |
| VIIa-9 | 2-naphthyl | 135–136° C. | C | 81.68 | 81.40 |
|  |  |  | H | 5.57 | 5.70 |
|  |  |  | N | 5.95 | 6.16 |
| VIIa-10 | 1-naphthyl | 123–125° C. | C | 81.68 | 81.61 |
|  |  |  | H | 5.57 | 5.83 |
|  |  |  | N | 5.95 | 6.16 |
| VIIa-11 | 2-thienyl | 59–60° C. | C | 62.80 | 62.61 |
|  |  |  | H | 4.74 | 4.74 |
|  |  |  | N | 7.33 | 7.64 |
| VIIa-12 | 3-pyridyl | oily | C | 70.95 | 71.06 |
|  |  |  | H | 5.41 | 5.28 |
|  |  |  | N | 7.52 | 7.32 |

TABLE 1-continued

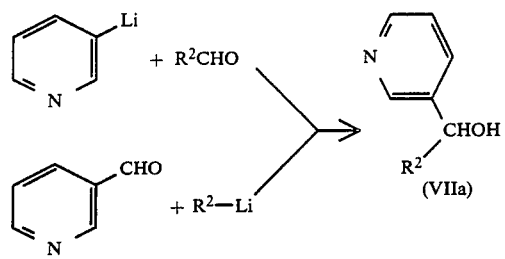

| Compound No. | R² | m.p. | Elemental Analysis Calc. | Found |
|---|---|---|---|---|
| VIIa-13 | 4-COOMe-phenyl | 150–152° C. | C 69.12<br>H 5.39<br>N 5.76 | 69.30<br>5.40<br>5.81 |
| VIIa-14 | 3,4,5-tri(OMe)-phenyl | 97–98° C. | C 65.44<br>H 6.22<br>N 5.09 | 65.37<br>6.20<br>5.15 |
| VIIa-15 | 2-F-phenyl | 86–87° C. | C 70.92<br>H 4.96<br>N 6.89 | 71.34<br>4.90<br>6.92 |
| VIIa-16 | 3-F-phenyl | 73–74° C. | C 70.92<br>H 4.96<br>N 6.89 | 70.83<br>4.95<br>6.81 |
| VIIa-17 | 3-CF₃-phenyl | oily | C 61.66<br>H 3.98<br>N 5.53 | 61.48<br>3.84<br>5.43 |
| VIIa-18 | 3-methylthienyl | oily | C 62.80<br>H 4.74<br>N 7.33 | 62.76<br>4.83<br>7.16 |
| VIIa-19 | 2-methylfuryl | oily | C 68.56<br>H 5.18<br>N 8.00 | 68.64<br>5.30<br>7.89 |
| VIIa-20 | (E)-5-(1-pentenyl)-2-methylthienyl | oily | C 69.46<br>H 6.61<br>N 5.40<br>S 12.36 | 69.63<br>6.38<br>5.62<br>12.43 |
| VIIa-21 | 3-pentylphenyl | oily | C 79.96<br>H 8.29<br>N 5.49 | 80.21<br>8.16<br>5.52 |
| VIIa-22 | 4-pentylphenyl | 76–77° C. | C 79.96<br>H 8.29<br>N 5.49 | 79.84<br>8.33<br>5.32 |

TABLE 1-continued $$\text{pyridyl-Li} + R^2CHO \quad \text{or} \quad \text{3-pyridyl-CHO} + R^2\text{-Li} \longrightarrow \underset{(VIIa)}{\text{3-pyridyl-CH(OH)-}R^2}$$

| Compound No. | $R^2$ | m.p. | Elemental Analysis Calc. | Found |
|---|---|---|---|---|
| VIIa-23 | (benzothiophene-2-yl with methyl) | 141–142° C. | C 69.68 | 69.77 |
| | | | H 4.59 | 4.40 |
| | | | N 5.80 | 5.72 |
| | | | S 13.29 | 13.40 |

REFERENCE EXAMPLE 2

An alcohol compound (VIIa) prepared in Reference Example 1 was led to a carbonyl compound (IIa in Table II) by Process A or Process B shown below.

Oxidation with manganese dioxide was able to apply to oxidation of all the secondary alcohol compounds (VII), and, oxidation with dimethylsulfoxide-oxalyl chloride could apply to all the compounds except those containing thiophene nuclei.

Process A

The alcohol compound (VIIa-11) (4.0 g, 21 mmoles) was dissolved in methylene chloride (70 ml). To the solution was added manganese dioxide (13 g), and the mixture was stirred for 10 hours under heating. Then, manganese dioxide was removed by filtration. The filtrate, combined with washings of the manganese dioxide with ethyl acetate and acetone, was concentrated. The concentrate was recrystallized from a mixture of isopropylether and ethyl acetate to give the corresponding carbonyl compound (IIa-12 in Table 2) (3 g, 75%).

Process B

Oxalyl chloride (2.2 ml) was dissolved in methylene chloride (50 ml), and the solution was cooled to −60° C., to which was added dropwise a methylene chloride solution (5 ml) containing dimethylsulfoxide (4 ml) at a temperature ranging from −60° C. to −50° C. To the mixture was further added dropwise a methylene chloride solution (50 ml) of alcohol compound (VII-2, 4.5 g, 20 mmoles) during 10 minutes at the same temperature range. Further 15 minutes, triethylamine (15 ml) was gradually added to the mixture, then the reaction temperature was raised up to room temperature taking about one hour. To the reaction mixture was added water (20 ml), and the solvent was evaporated off. The residue was subjected to extraction with ethyl acetate. The organic layer was washed with water, dried and concentrated under reduced pressure. The concentrate was purified by means of silica-gel chromatography to yield the corresponding carbonyl compound (IIa-3 in Table 2, 4.3 g, 98%).

By the procedure analogous to the above two processes, the carbonyl compounds shown in Table 2 below were prepared (IIa-1–IIa-25, in Table 2).

TABLE 2

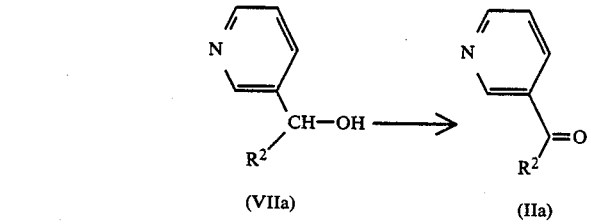

| Compound No. | $R^2$ | m.p. | Elemental Analysis Calc. | Found |
|---|---|---|---|---|
| IIa-1 | 4-methylphenyl (–C₆H₄–Me) | 77–78° C. | C 79.16 | 79.21 |
| | | | H 5.62 | 5.37 |
| | | | N 7.10 | 6.99 |
| IIa-2 | 4-methoxyphenyl (–C₆H₄–OMe) | 98–99° C. | C 73.22 | 72.94 |
| | | | H 5.20 | 5.15 |
| | | | N 6.57 | 6.52 |

TABLE 2-continued (VIIa) → (IIa)

| Compound No. | R² | m.p. | Elemental Analysis Calc. | Found |
|---|---|---|---|---|
| IIa-3 | 4-isopropylphenyl | oily | C 79.97<br>H 6.71<br>N 6.22 | 79.79<br>6.84<br>6.20 |
| IIa-4 | 4-bromophenyl | oily | C 54.99<br>H 3.08<br>N 5.35 | 54.78<br>3.14<br>5.22 |
| IIa-5 | 3-bromophenyl | 57–58° C. | C 54.99<br>H 3.08<br>N 5.35 | 54.82<br>3.21<br>5.42 |
| IIa-6 | 2-bromophenyl | oily | C 54.99<br>H 3.08<br>N 5.35 | 55.07<br>3.10<br>5.26 |
| IIa-7 | 3-methoxy-4-propoxyphenyl | 117–118° C. | C 70.83<br>H 6.31<br>N 5.16 | 70.74<br>6.43<br>5.09 |
| IIa-8 | 3-methoxy-2-propoxyphenyl | oily | C 70.83<br>H 6.31<br>N 5.16 | 70.89<br>6.34<br>5.23 |
| IIa-9 | 3,4-methylenedioxyphenyl | 112–113° C. | C 68.82<br>H 3.99<br>N 6.17 | 68.86<br>3.95<br>6.28 |
| IIa-10 | 2-naphthyl | 71–72° C. | C 82.38<br>H 4.75<br>N 6.01 | 82.33<br>4.80<br>5.99 |
| IIa-11 | 1-naphthyl | oily | C 82.38<br>H 4.75<br>N 6.01 | 82.46<br>4.82<br>6.11 |
| IIa-12 | 2-thienyl | 93–94° C. | C 63.47<br>H 3.73<br>N 7.40 | 63.97<br>3.88<br>7.36 |

TABLE 2-continued
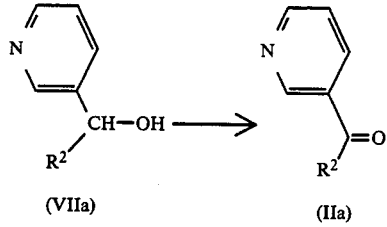
| Compound No. | R² | m.p. | Elemental Analysis Calc. | Found |
|---|---|---|---|---|
| IIa-13 | 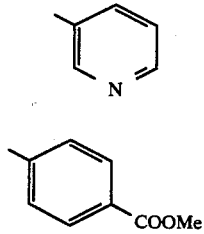 | 115–116° C. | C 71.73<br>H 4.38<br>N 15.21 | 71.81<br>4.34<br>15.11 |
| IIa-14 | 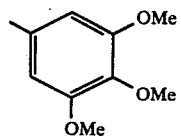 | 144–145° C. | C 69.70<br>H 4.60<br>N 5.81 | 69.77<br>4.51<br>6.06 |
| IIa-15 | 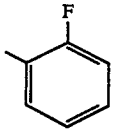 | oily | C 65.92<br>H 5.53<br>N 5.13 | 66.12<br>5.43<br>5.08 |
| IIa-16 | 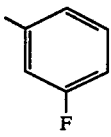 | oily | C 71.64<br>H 4.01<br>N 6.96 | 71.73<br>4.03<br>6.87 |
| IIa-17 | 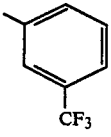 | 45–46° C. | C 71.64<br>H 4.01<br>N 6.96 | 71.64<br>4.11<br>6.45 |
| IIa-18 | 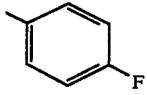 | oily | C 62.16<br>H 3.21<br>N 5.58 | 62.21<br>3.16<br>5.64 |
| IIa-19 | 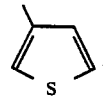 | oily | C 71.64<br>H 4.01<br>N 6.96 | 71.68<br>4.13<br>6.92 |
| IIa-20 | 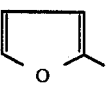 | 74–75° C. | C 63.47<br>H 3.73<br>N 7.40 | 63.32<br>3.85<br>7.22 |
| IIa-21 | 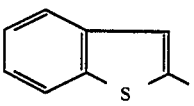 | 57–58° C. | C 69.36<br>H 4.07<br>N 8.09 | 69.28<br>4.10<br>8.16 |
| IIa-22 |  | 94–95° C. | C 70.27<br>H 3.79<br>N 5.85<br>S 13.40 | 70.35<br>3.68<br>5.92<br>13.34 |

TABLE 2-continued

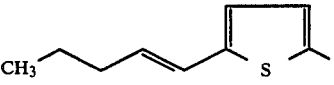

(VIIa) → (IIa)

| Compound No. | R² | m.p. | Elemental Analysis Calc. | Found |
|---|---|---|---|---|
| IIa-23 | 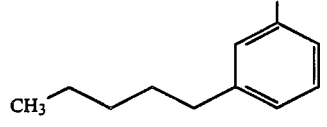 | oily | C 70.01<br>H 5.88<br>N 5.44<br>S 12.46 | 69.87<br>5.92<br>5.38<br>12.58 |
| IIa-24 | 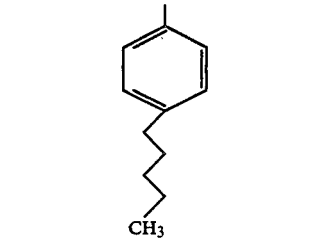 | oily | C 80.61<br>H 8.36<br>N 5.53 | 80.69<br>8.35<br>5.42 |
| IIa-25 |  | oily | C 80.61<br>H 8.36<br>N 5.53 | 80.53<br>8.48<br>5.41 |

EXAMPLE 1

To dimethylsulfoxide (40 ml) was added dropwise sodium hydride (1.0 g), and the mixture was heated at 80° C. for 30 minutes. The reaction mixture was cooled to room temperature, to which was added 5-carboxypentyltriphenyl phosphonium bromide (9.5 g, 21 mmoles) and the mixture was stirred for 5 minutes. To the reaction mixture was added a tetrahydrofuran solution (10 ml) of 3.7 g (0.02 mole) of 3-benzoylpyridine. The mixture was stirred for 30 minutes at room temperature, followed by addition of water (100 ml), which was subjected to extraction twice with ethylacetate (50 ml). The aqueous layers were combined and adjusted to pH 6 with 2N HCl, which was subjected to extraction with ethyl acetate. The organic layers were combined and washed with water and dried (magnesium sulfate). The solvent was then evaporated off, and the residue was subjected to silica-gel chromatography, using ethanolethyl acetate (1:5) as eluant to yield (E)+(Z)-7-(3-pyridyl)-7-phenyl-6-heptenoic acid (Ia-3, Ia-4 in Table 3) (4.5 g 79%).

By the procedure analogous to the above Example, (Ia-1–Ia-10) in Table 3-1, (Ib-11–Ib-38) in Table 3-2, (Ic-39–Ic-41) in Table 3-3, and (Id-42) in Table 3-4 were prepared.

Separation of isomers was conducted by means of fractional crystallization or a liquid chromatography using Lobar Lichroprep RP-8 (40–63 μm, manufactured by Merck & Co.).

TABLE 3-1

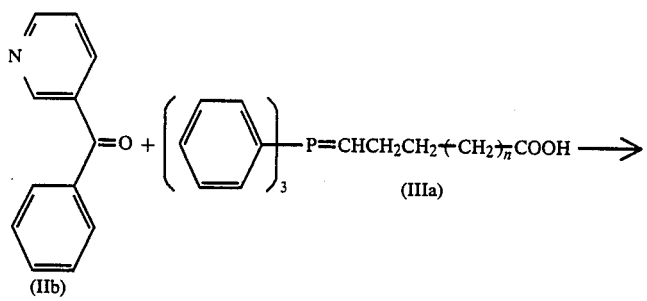

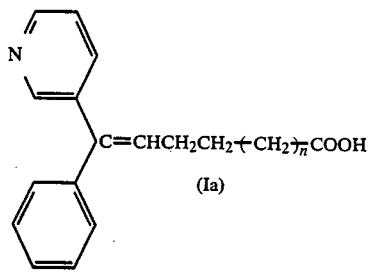

| Compound No. | n | Isomer*[1] (m.p.) | NMR Spectrum (δ value, p.p.m., TMS internal standard) |
|---|---|---|---|
| Ia-1 | 1 | Z | 11.1 (1H,COOH), 8.53 (1H, m), 8.45 (1H,m), 7.20 (7H,m), 6.17 (1H,t,7Hz), 2.32 (2H,m), 2.17 (2H,m), 1.79 (2H,m) |
| Ia-2 | 1 | E | 11.1 (1H,COOH), 8.53(1H,m), 8.45 (1H,m), 7.20 (7H,m), 6.12 (1H,t,7Hz), 2.32 (2H,m), 2.17 (2H,m), 1.79 (2H,m) |
| Ia-3 | 2 | Z | 11.6 (1H,COOH), 8.53 (1H,m), 8.46 (1H,m), 7.54 (1H,d,7Hz), 7.27 (6H,m), 6.16 (1H,t,7Hz), 2.29 (2H,t,7Hz), 2.17 (2H,m), 1.57 (4H,m) |
| Ia-4 | 2 | E 108–110° C. | 11.8 (1H,COOH), 8.55 (2H,m), 7.46 (1H,d,7Hz), 7.31 (3H,m), 7.16 (3H,m), 6.13 (1H,t,7Hz), 2.29 (2H,t,7Hz), 2.13 (2H,t,7Hz), 1.58 (4H,m) |
| Ia-5 | 3 | Z | 9.43 (1H,COOH), 8.50 (2H,m), 7.52 (1H,d,6Hz), 7.20 (6H,m), 6.16 (1H,t,7Hz), 2.31 (2H,t,7Hz), 2.06 (2H,t,7Hz), 1.60 (2H,m), 1.43 (4H,m) |
| Ia-6 | 3 | E | 11.30 (1H,COOH), 8.53 (1H,s), 8.43 (1H,d,5Hz), 7.47 (1H,d,7Hz), 7.30 (3H,m), 7.20 (3H,m), 6.11 (1H,t,7Hz), 2.10 (2H,t,7Hz), 1.60 (2H,m), 1.43 (4H,m) |
| Ia-7 | 4 | Z | 11.03 (1H,COOH), 8.52 (1H,s), 8.43 (1H,d,5Hz), 7.47 (1H,d,7Hz), 7.30 (3H,m), 7.20 (3H,m), 6.11 (1H,t,7Hz), 2.30 (2H,m), 2.10 (2H,m), 1.7–1.3 (8H,m) |
| Ia-8 | 4 | E | 10.90 (1H,COOH), 8.50 (2H,m), 7.48 (2H,m), 7.20 (5H,m), 6.17 (1H,t,8Hz), 2.31 (2H,t,7Hz), 2.07 (2H,t,7Hz), 1.7–1.3 (8H,m) |
| Ia-9 | 5 | Z | 10.70 (1H,COOH), 8.46 (2H,m), 7.46 (2H,m), 7.20 (5H,m), 6.16 (1H,t,8Hz), 2.31 (2H,t,7Hz), 2.04 (2H,t,7Hz), 1.60 (2H,m), 1.28 (10H,m) |
| Ia-10 | 5 | E | 10.63 (COOH), 8.49 (2H,m), 7.27 (7H,m), 6.12 (1H,t,7Hz), 2.31 (2H,t,7Hz), 2.08 (2H,t,7Hz), 1.58 (2H,m), 1.28 (10H,m) |

*[1] In the designation of isomers, E means the isomers where the pyridine nucleus on the one carbon and hydrogen atom on the other carbon are on the same direction in the tri-substituted olefin bond, and Z means the isomers where they are on opposite directions to each other. The same applies to the subsequent Tables.

TABLE 3-2

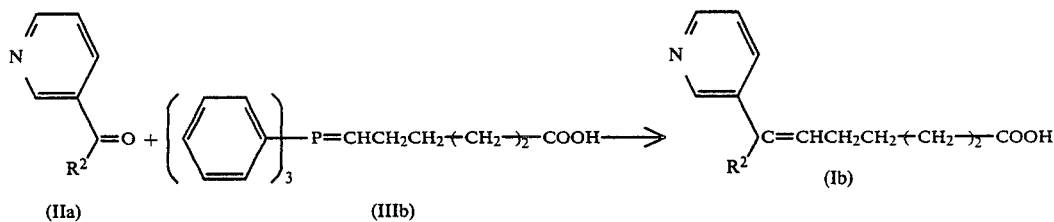

| Compound No. | R² | Isomer*¹ (m.p.) | NMR Spectrum (δ value, p.p.m., TMS internal standard) |
|---|---|---|---|
| Ib-11 | 4-Me-C₆H₄- | A | 10.55 (COOH,1H), 8.55 (1H,s), 8.43 (1H,d,6Hz), 7.47 (1H,d,8Hz), 7.18 (2H,d,9Hz), 7.18 (1H,m), 7.00 (2H,d,9Hz), 6.09 (1H,t,7Hz), 2.37 (3H,s), 2.30 (2H,t,7Hz), 2.18 (2H,t,7Hz), 1.61 (4H,m) |
| Ib-12 | 4-Me-C₆H₄- | B (126–127° C.) | 10.79 (1H,COOH), 8.56 (1H,d,6Hz), 8.44 (1H,s), 7.54 (1H,d,t,8 and 2Hz), 7.32 (1H,d,d,8 and 6Hz), 7.05 (4H,s), 6.13 (1H,t,7Hz), 2.30 (3H,s), 2.21 (2H,t), 2.06 (2H,t), 1.61 (4H,t) |
| Ib-13 | 2-naphthyl | A | 10.40 (1H,COOH), 8.61 (1H,m), 8.45 (1H,m), 7.50 (9H,m), 6.21 (1H,t,7Hz), 2.29 (4H,m), 1.60 (4H,m) |

| Compound No. | R² | Isomer*² (m.p.) | NMR Spectrum |
|---|---|---|---|
| Ib-14 | 2-naphthyl | B (157–158° C.) | 11.26 (1H,COOH), 8.60 (1H,m), 8.54 (1H,m), 7.52 (3H,m), 7.44 (6H,m), 6.30 (1H,t,7Hz), 2.31 (2H,m), 2.12 (2H,m), 1.60 (4H,m) |
| Ib-15 | 4-OMe-C₆H₄- | A + B | 10.50 (1H,COOH), 8.51 (1H,m), 8.43 (1H,m), 7.00 (6H,m), 6.07 (1H,t,7Hz), 2.29 (2H,t), 2.14 (2H,t), 1.56 (4H,m), 3.79 & 3.74 (3H,s) |
| Ib-16 | 3,4-methylenedioxyphenyl | A | 10.30 (1H,COOH), 8.50 (2H,m), 7.47 (2H,m), 6.80 (1H,d,8Hz), 6.60 (1H,d,d,8 & 2Hz), 6.57 (1H,d,2Hz), 6.06 (1H,t,7Hz), 5.96 (2H,s), 2.31 (2H,m), 2.16 (2H,m), 1.58 (4H,m) |
| Ib-17 | 3,4-methylenedioxyphenyl | B (90–91° C.) | 9.20 (1H,COOH), 8.46 (2H,m), 7.50 (1H,m), 7.37 (1H,m), 6.68 (1H,d,2Hz), 6.68 (1H,d,8Hz), 6.53 (1H,d,d,8 & 2Hz), 6.05 (1H,t,7Hz), 5.92 (2H,s), 2.28 (2H,m), 2.03 (2H,m), 1.57 (4H,m) |

TABLE 3-2-continued $$\text{(IIa)} \quad + \quad \text{(IIIb)} \quad \longrightarrow \quad \text{(Ib)}$$

Structures:
- (IIa): 3-pyridyl–C(=O)–R²
- (IIIb): (phenyl)₃P=CHCH₂CH₂(CH₂)₂–COOH
- (Ib): 3-pyridyl–C(R²)=CHCH₂CH₂(CH₂)₂–COOH

| Compound No. | R² | | NMR Spectrum (δ value, p.p.m., TMS internal standard) |
|---|---|---|---|
| Ib-18 | 4-(isopropyl)phenyl (–C₆H₄–CH(Me)₂) | A | 9.07 (1H,COOH), 8.50 (2H,m), 7.44 (1,d,7Hz), 7.20 (2H,d,8Hz), 7.18 (1H,m), 7.02 (2H,d,8Hz), 6.08 (1H,t.7Hz), 2.92 (1H,m), 2.31 (2H,m), 2.16 (2H,m), 1.57 (4H,m), 1.27 (6H,d,7Hz) |
| Ib-19 | 4-(isopropyl)phenyl | B | 10.60 (1H,COOH), 8.53 (1H,m), 8.45 (1H,m), 7.50 (1H,m), 7.20 (1H,m), 7.09 (4H,s), 6.13 (1H,t,7Hz), 2.86 (1H,m), 2.22 (2H,m), 2.06 (2H,m), 1.57 (4H,m), 1.23 (6H,d,7Hz) |
| Ib-20 | 2-thienyl | B (84–85° C.) | 10.50 (1H,COOH), 8.59 (1H,d,2Hz), 8.48 (1H,d,d,2 & 4Hz), 7.58 (1H,d,t,7 & 2Hz), 7.29 (1H,m), 7.24 (1H,d,d,4 & 7Hz), 7.04 (1H,m), 6.85 (1H,m), 6.04 (1H,t,8Hz), 2.34 (4H,m), 1.64 (4H,m) |
| Ib-21 | 2-thienyl | A (93–94° C.) | 11.90 (1H,COOH), 8.53 (2H,m), 7.62 (1H,m), 7.20 (1H,m), 7.15 (1H,m), 6.85 (1H,m), 6.48 (1H,m), 6.22 (1H,t,7Hz), 2.35 (4H,m), 1.63 (4H,m) |
| Ib-22 | 1-naphthyl | A | 11.80 (1H,COOH), 8.64 (1H,m), 8.38 (1H,m), 7.79 (2H,m), 7.60 (1H,m), 7.38 (6H,m), 6.50 (1H,t,7Hz), 2.20 (2H,m), 1.87 (2H,m), 1.49 (4H,m) |
| Ib-23 | 2-bromophenyl | A | 10.15 (1H,COOH), 8.64 (1H,m), 8.38 (1H,m), 7.79 (2H,m), 7.60 (1H,m), 7.38 (6H,m), 6.50 (1H,t,7Hz), 2.20 (2H,m), 1.87 (2H,m), 1.49 (4H,m) |
| Ib-24 | 3-pyridyl | — | 10.85 (1H,COOH), 8.51 (4H,m), 7.43 (4H,m), 6.25 (1H,t,7Hz), 2.27 (4H,m), 1.59 (4H,m) |
| Ib-25 | 2-propoxy-3-methoxyphenyl | A | 10.12 (1H,COOH), 8.57 (1H,d,2Hz), 8.40 (1H,d,d,4 & 2Hz), 7.46 (1H,d,t,8 & 2Hz), 7.10 (3H,m), 6.68 (1H,d,d,7 & 2Hz), 6.19 (1H,t,7Hz), 3.84 (3H,s), 3.64 (2H,t,7Hz), 2.29 (2H,m), 2.25 (2H,m), 1.52 (4H,m), 0.76 (3H,t,7Hz) |
| Ib-26 | 4-bromophenyl | A + B | 10.62 (1H, COOH), 8.50 (2H,m), 7.40 (6H,m), 6.13 & 6.17 (1H,t), 2.32 (2H,m), 2.10 (2H,m), 1.57 (4H,m) |

TABLE 3-2-continued

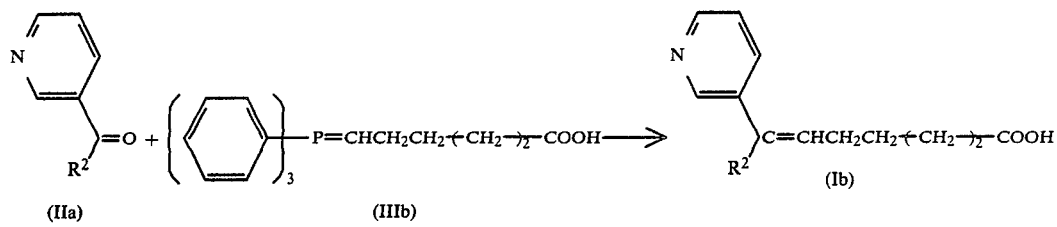

(IIa)　　　　　(IIIb)　　　　　　　　　　(Ib)

| Compound No. | R² | | NMR Spectrum (δ value, p.p.m., TMS internal standard) |
|---|---|---|---|
| Ib-27 | 3-Br-phenyl | A + B | 11.50 (1H,COOH), 8.48 (2H,m), 7.30 (6H,m), 6.18 & 6.14 (1H,t,7Hz), 2.30 (2H,m), 2.15 (2H,m), 1.57 (4H,m) |
| Ib-28 | 2-F-phenyl | A | 12.70 (1H,COOH), 8.47 (2H,m), 7.45 (1H,m), 7.20 (4H,m), 6.28 (1H,t,8Hz), 2.29 (2H,m), 1.59 (4H,m) |
| Ib-29 | 3-F-phenyl | A + B | 11.85 (1H,COOH), 8.50 (2H,m), 7.16 (4H,m), 6.90 (2H,m), 6.20 & 6.14 (1H,t,7Hz), 2.23 (2H,m), 2.10 (2H,m), 1.58 (4H,m) |
| Ib-30 | 4-F-phenyl | A + B | 11.28 (1H,COOH), 8.50 (2H,m), 7.40 (2H,m), 7.00 (4H,m), 6.12 & 6.09 (1H,t,7Hz), 2.30 (2H,m), 2.13 (2H,m), 1.57 (4H,m) |
| Ib-31 | 3-CF₃-phenyl | A + B | 11.70 (1H,COOH), 8.50 (2H,m), 7.40 (6H,m), 6.22 & 6.20 (1H,t), 2.30 (2H,m), 2.11 (2H,m), 1.60 (4H,m) |
| Ib-32 | 3-OMe-4-OPr-phenyl | A + B | 9.77 (1H,COOH), 8.50 (2H,m), 7.40 (2H,m), 6.70 (3H,m), 6.08 (1H,t,7Hz), 3.93 (2H,t,8Hz), 3.78 (3H,s), 2.28 (2H,m), 2.05 (2H,m), 1.79 (2H,m), 1.59 (4H,m), 1.01 (3H,t,8Hz) |
| Ib-33 | 2-thienyl | A + B | 11.60 (1H,COOH), 8.48 (2H,m), 7.30 (4H,m), 6.98 & 6.87 (1H,m), 6.21 & 6.06 (1H,t,7Hz), 2.28 (4H,m), 1.59 (4H,m) |
| Ib-34 | 2-furyl | A + B | 9.6 (1H,COOH), 8.40–8.70 (2H,m), 7.20–7.75 (3H,m), 6.10–6.50 (2H,m), 5.65–5.90 (1H,m), 1.90–2.70 (4H,m), 1.30–1.90 (4H,m) |
| Ib-35 | benzo[b]thiophen-2-yl | A (145–146° C.) | 11.87 (1H,COOH), 8.43 (1H), 7.20–8.00 (6H,m), 6.73 (1H,s), 6.33 (1H,t), 2.07 (4H,m), 1.43 (4H,m) |
| Ib-36 | 5-(1-pentenyl)-2-thienyl (—CH=CH—C₃H₇) C₅H₉ | A + B | 11.80 (1H,COOH), 8.40–8.70 (2H,m), 7.20–7.90 (2H,m), 5.30–6.90 (5H,m), 2.00–2.60 (6H,m), 1.20–1.90 (6H,m), 0.90 (3H,t) |

TABLE 3-2-continued

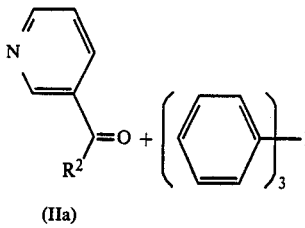

(IIa) + (IIIb) → (Ib)

| Compound No. | R² | | NMR Spectrum (δ value, p.p.m., TMS internal standard) |
|---|---|---|---|
| Ib-37 | 3-C₅H₁₁-phenyl | A + B | 10.20 (1H,COOH), 8.40–8.70 (2H,m), 6.85–7.60 (6H,m), 6.00–6.30 (1H,m), 1.90–2.70 (6H,m), 1.20–1.90 (10H,m), 0.87 (3H,t) |
| Ib-38 | 4-C₅H₁₁-phenyl | A + B | 9.40 (1H,COOH), 8.35–8.65 (2H,m), 6.90–7.90 (6H,m), 5.90–6.30 (1H,m), 2.00–2.70 (6H,m), 1.20–1.90 (10H,m), 0.90 (3H,t) |

*²: Two types of geometrical isomers are optionally designated by A and B, and a mixture of them is designated as A + B. This designation is applied in subsequent tables.

TABLE 3-3

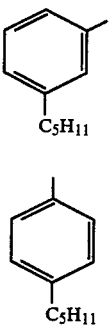 (Ic)

| Compound No. | R¹ | Isomer *2 (m.p.) | NMR Spectrum (δ value, p.p.m., TMS internal standard) |
|---|---|---|---|
| Ic-39 | 2-pyridyl | A | 1.53(4H), 2.15(4H), 6.13(1H), 7.10–7.80(8H), 8.68(1H), 10.33(1H) |
| Ic-40 | 2-pyridyl | B | 1.57(4H), 2.20(4H), 6.80(1H), 6.83(1H), 7.00–7.65(7H), 8.60(1H), 9.60(1H) |
| Ic-41 | 4-pyridyl | A (149–150°) | 1.47(4H), 2.13(4H), 6.37(1H), 7.00–7.60(7H), 8.40(2H), 11.85(1H) |

*2: Refer to Table 3-2

TABLE 3-4

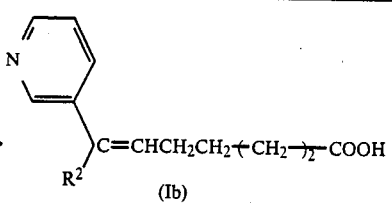 (Id)

| Compound No. | R² | Isomer *2 (m.p.) | NMR Spectrum (δ value, p.p.m., TMS internal standard) |
|---|---|---|---|
| Id-42 | 2-methylthienyl | A + B | 11.80 (1H,COOH), 8.53 (2H,m), 7.62 (1H,m), 7.30 (2H,m), 6.85 (1H,m), 6.83 and 6.48 (1H,m), 6.22 and 6.04 (1H,t,7Hz), 2.30 (4H,m), 1.46 (6H,m) |

*2: Refer to Table 3-2

EXAMPLE 2

Phosphorus pentachloride (3.0 g, 14.2 mmoles) was suspended in dichloromethane (4 ml). To the suspension was added dropwise a solution of 1-phenyl-1-(3-pyridyl)-2-propen-1-ol (2.0 g, 9.5 mmoles) in dichloromethane (20 ml) at 0° C., then the mixture was stirred for one hour at room temperature, followed by washing with water, saturated aqueous solution of sodium hydrogen carbonate in the order. The organic layer is dried (magnesium sulfate), and concentrated to about 20 ml at a temperature not exceeding 30° C. The solution was further dried with molecular sieves 4A. This solution was named as (a) solution. Separately, sodium hydride (400 mg, 10 mmoles) is suspended in dimethylformamide (5 ml). To the suspension was added dropwise methyl metahydroxybenzoate (1.37 g, 9.0 mmoles) dissolved in dimethylformamide (5 ml). The mixture was stirred for 30 minutes at 0° C., to which was added dropwise the (a) solution, followed by stirring at room temperature for 1.5 hours. The reaction mixture was poured in ice-water, which is subjected to extraction with ethyl acetate, washed with water and dried (magnesium sulfate), followed by removing the solvent by evaporation under reduced pressure. The residue was subjected to silica-gel column chromatography, using ether-ethyl acetate (7:3) as eluant to yield methyl 3-[3-(3-pyridyl)-3-phenyl-2-propenyloxy]benzoate (If-56) (3.0 g, 92%).

Substituted vinyl carboxylic acid derivatives (I) prepared by a procedure analogous to that of the above Example 2 are shown as (Ie-43, Ie-44, Ie-52) in Table 4-1, (If-55–IF-63) in Table 4-2 and (Ii-77 and Ii-78) in Table 6.

EXAMPLE 3

Methyl 3-[3-(3-pyridyl)-3-phenyl-2-propenyloxy]benzoate (If-56, 1.5 g, 4.35 mmoles) was dissolved in a mixture of water (3 ml) and methanol (10 ml). To the solution was added sodium hydroxide (700 mg, 17.5 mmoles). The mixture was stirred for 2 hours at 60° C., which was then left standing for cooling. To the reaction solution was added water, the pH of which was adjusted to 5 with 1N hydrochloric acid, followed by extraction with ethyl acetate. The organic layer was washed with saturated saline, dried and the solvent was evaporated off. The residue was subjected to silica-gel column chromatography using ethyl acetate as eluant to yield 3-[3-(3-pyridyl)-3-phenyl-2-propenyloxy]benzoic acid (Ie-46) (1.15 g, 80%). Hydrolysis analogous to the above afforded substituted vinyl carboxylic acid derivatives (Ie-45–Ie-51, Ie-53, Ie-54) shown in Table 4-1.

EXAMPLE 4

To (E)-7-(3-pyridyl)-7-phenyl-6-heptenoic acid (Ia-4, 300 mg was dissolved in 2N HCl (5 ml). The solution was concentrated under reduced pressure. Recrystallization of the resulting crystals from ethanol-isopropyl ether gave (E)-7-(3-pyridyl)-7-phenyl-6-heptenoic acid hydrochloride (Ii-75) (285 mg), m.p. 163°–165° C. Physicochemical properties including other data are shown in Table 6.

EXAMPLE 5

(E)-7-(3-pyridyl)-7-phenyl-6-heptenoic acid (Ia-4) (500 mg) and sodium hydrogen carbonate (160 mg) were added to water (5 ml) to make a homogeneous solution. The solution was concentrated under reduced pressure. The concentrate was pulverized by the use of ethanol-isopropylether to obtain sodium (E)-7-(3-pyridyl)-7-phenyl-6-heptenoate (Ii-76, 300 mg). The physico-chemical properties and other data of the product are shown in Table 6.

EXAMPLE 6

(E+Z)-7-(3-pyridyl)-7-phenyl-6-heptenoic acid (Ia-3, Ia-4) (0.5 g) was dissolved in ethyl acetate (50 ml). To the solution was added, under cooling, a diazomethane ether solution, which was concentrated, and the concentrate was subjected to a Lobar column-chromatography (RP-8) to separate into methyl (E)- and methyl (Z)-7-(3-pyridyl)-7-phenyl-6-heptenoate (Ig-72) and Ig-73), respectively.

The reaction process analogous to Example 6 gave substituted vinyl carboxylic acid derivatives (Ig-64–Ig-74). The physico-chemical properties of these compounds, including other physical constants thereof, are shown in Table 5.

TABLE 4-1

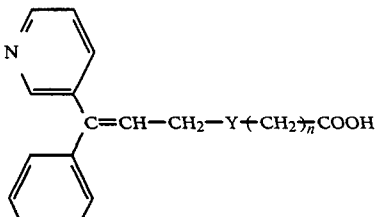

(Ie)

| Compound No. | Y | n | Isomer *2 (m.p.) | NMR Spectrum (δ value, p.p.m., TMS internal standard) |
|---|---|---|---|---|
| Ie-43 | S | 1 | A (132–133° C.) | 2.93 (2H), 3.38 (2H), 6.27 (1H), 7.10–7.50 (6H), 7.65 (1H), 8.40–8.60 (2H), 12.72 (1H) |
| Ie-44 | S | 2 | A (147–148° C.) | 2.38 (2H), 2.70 (2H), 3.22 (2H), 6.23 (1H), 7.10–7.50 (6H), 7.62 (1H), 8.48 (1H), 10.52 (1H) |
| Ie-45 | O— (2-methylphenyl) | 0 | A | 4.78 (2H), 6.43 (1H), 6.70–7.70 (10H), 8.07 (1H), 8.40–9.00 (3H) |
| Ie-46 | O— (3-methylphenyl) | 0 | A | 4.62 (2H), 6.40 (1H), 6.90–7.80 (11H), 8.57 (1H), 8.67 (1H), 11.40 (1H) |
| Ie-47 | O— (4-methylphenyl) | 0 | A (170–172° C.) | 4.95 (2H), 6.33 (1H), 6.83 (2H), 7.10–7.70 (7H), 7.98 (2H), 8.40–8.80 (2H), 10.18 (1H) |
| Ie-48 | O—, OH (disubstituted) | 0 | A (195–200° C.) | 4.92 (2H), 6.45 (1H), 7.10–7.70 (9H), 8.42 (1H), 8.57 (1H), 9.70 (1H) |
| Ie-49 | O— (2-methylphenyl) | 1 | A (162–163° C.) | 3.50 (2H), 4.53 (2H), 6.40 (1H), 6.70–7.70 (11H), 8.40 (1H), 8.57 (1H) |
| Ie-50 | O— (3-methylphenyl) | 1 | A (146–147° C.) | 3.47 (2H), 4.53 (2H), 6.40 (1H), 6.65–6.90 (2H), 7.00–7.70 (9H), 8.25–8.70 (2H), |
| Ie-51 | O— (4-methylphenyl) | 1 | A (194–195° C.) | 3.40 (2H), 4.50 (2H), 6.40 (1H), 6.65–6.90 (2H), 7.00–7.70 (9H), 8.30–8.70 (2H), 12.10 (1H) |
| Ie-52 | S | 2 | B | 2.63 (2H), 2.73 (2H), 3.20 (2H), 6.22 (1H), 6.77 (1H), 7.10–7.50 (6H), 7.60 (1H), 8.40–8.70 (2H) |

TABLE 4-1-continued

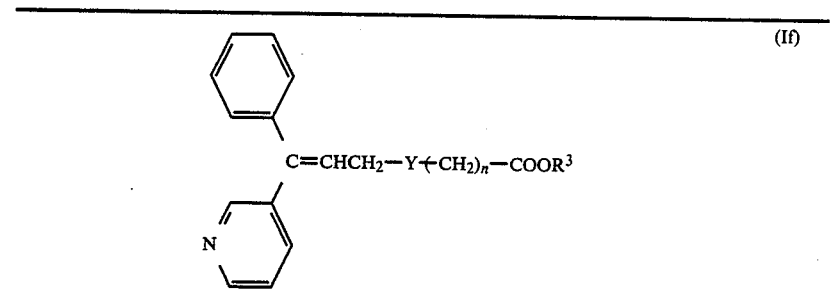

(Ie)

| Compound No. | Y | n | Isomer *2 (m.p.) | NMR Spectrum (δ value, p.p.m., TMS internal standard) |
|---|---|---|---|---|
| Ie-53 | | 0 | A (120–126° C.) | 4.60 (2H), 6.30–6.55 (3H), 7.10–7.80 (8H), 8.40 (1H), 8.57 (1H) |
| Ie-54 | | 0 | A (218–219° C.) | 4.50 (2H), 6.37 (1H), 6.87 (1H), 6.95–7.65 (9H), 9.60 (2H) |

(If)

Structure: Ph\C=CHCH₂—Y(CH₂)ₙ—COOR³ with 3-pyridyl

| Compound No. | Y | n R³ | Isomer*2 (m.p.) | NMR Spectrum (δ value, p.p.m., TMS internal standard) |
|---|---|---|---|---|
| If-55 | o-tolyloxy | 0 Me | A (92–93° C.) | 3.88 (3H), 4.65 (2H), 6.47 (1H), 6.70–7.90 (11H), 8.50 (1H), 8.60 (1H) |
| If-56 | m-tolyloxy | 0 Me | A + B | 3.87 (3H), 4.60 (2H), 6.40 (1H), 6.90–7.70 (11H), 8.53 (1H), 8.62 (1H) |
| If-57 | p-tolyloxy | 0 Me | A + B | 3.83 (3H), 4.60 (2H), 6.38 (1H), 6.82 (2H), 7.10–7.65 (7H), 7.93 (2H), 8.52 (1H), 8.60 (1H) |
| If-58 | 2-hydroxyphenoxy | 0 Et | A (141–142° C.) | 1.27 (3H), 4.20 (2H), 4.58 (2H), 6.40 (1H), 6.681 (1H), 7.10–7.70 (9H), 8.38 (1H), 8.53 (1H), 9.83 (1H) |
| If-59 | o-tolyloxy | 1 Me | A | 3.67 (5H), 4.58 (2H), 6.38 (1H), 6.60–7.70 (11H), 8.50 (1H), 8.62 (1H) |
| If-60 | m-tolyloxy | 1 Me | A | 3.57 (2H), 3.67 (3H), 4.58 (2H), 6.43 (1H), 6.60–6.90 (3H), 7.05–7.60 (8H), 8.56 (1H), 8.63 (1H) |

-continued
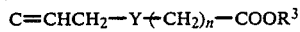
(If)
| Compound No. | Y | n R³ | Isomer*² (m.p.) | NMR Spectrum (δ value, p.p.m., TMS internal standard) |
|---|---|---|---|---|
| If-61 | 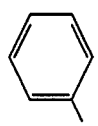 | 1 Me | A | 3.53 (2H), 3.67 (3H), 4.53 (2H), 6.42 (1H), 6.77 (2H), 7.00–7.60 (9H), 8.47 (1H), 8.60 (1H) |
| If-62 | 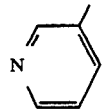 | 0 Me | A | 3.83 (3H), 4.57 (2H), 6.30–6.50 (3H), 7.15–7.80 (8H), 8.50 (1H), 8.60 (1H), 10.87 (1H) |
| If-63 | | 0 Me | A | 3.90 (3H), 4.52 (2H), 6.37 (1H), 6.75–7.60 (10H), 8.50 (1H), 8.60 (1H), 10.33 (1H) |
*²Refer to Table 3-2
TABLE 5
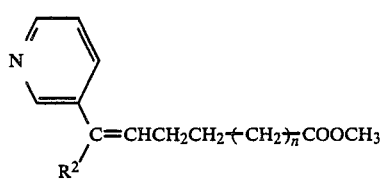
(Ig)
| Compound No. | R² | n | Isomer*¹, *² | NMR Spectrum (δ value, p.p.m; TMS internal standard) |
|---|---|---|---|---|
| Ig-64 | (4-OMe-phenyl) | 2 | A + B | 8.50 (2H,m), 7.30 (2H,m), 7.09 & 7.06 (2H,d,8Hz), 6.88 & 6.78 (2H,d,8Hz), 6.05 & 6.02 (1J,6), 3.82 & 3.78 (3H,s), 3.64 (3H,s), 2.26 & 2.13 (2H,m), 1.55 (4H,m) |
| Ig-65 | (3-OMe, 2-OPr phenyl) | 2 | A + B | 8.54 (1H,m), 8.40 (1H,m), 7.46 (1H,d,t, 7 & 2Hz), 7.12 (1H, d,d,7. & 4Hz), 6.90 (3H,m), 6.15 (1H,t, 7Hz), 3.84 (3H,s), 3.67 (3H,s), 3.64 (2H,m), 2.27 & 2.05 (2H,m), 1.51 (6H,m), 0.78 (3H, t,8Hz) |

TABLE 5-continued

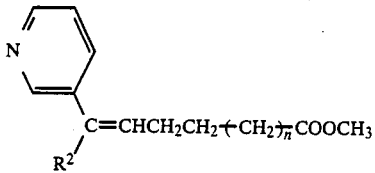
(Ig)

| Compound No. | R² | n | Isomer*1, *2 | NMR Spectrum (δ value, p.p.m; TMS internal standard) |
|---|---|---|---|---|
| Ig-66 | 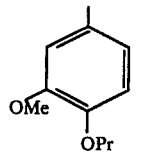 | 2 | A + B | 8.46 & 8.53 (1H,m), 7.40 (2H,m), 6.72 (3H,m) 6.06 & 6.04 (1H,t,7Hz), 3.94 & 4.00 (2H,t,7Hz), 3.18 & 3.64(3H,s), 2.25 & 2.05 (2H,m), 1.80 (6H,m), 1.04 & 1.00 (3H,t,m) |
| Ig-67 | 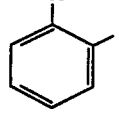 | 2 | A + B | 8.49 (2H,m), 7.49 & 7.30 (1H,m), 6.37 (2H,s), 6.10 & 6.08 (1H,t,7Hz), 3.82 (3H,s), 3.80 (3H,s), 3.77 (3H,s), 3.65 (3H,s), 2.27 & 2.15 (2H,m), 1.59 (4H,m) |
| Ig-68 | 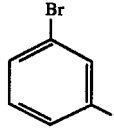 | 2 | A | 8.47 (2H,m), 7.64 (1H,m), 7.25 (5H,m), 6.24 (1H,t,7Hz), 3.62 (3H,s), 2.25 (2H,m), 2.02 (2H,m), 1.56 (4H,m) |
| Ig-69 | 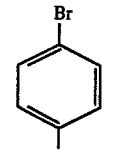 | 2 | A + B | 8.50 (2H,m), 7.30 (6H,m), 6.14 & 6.10 (1H,t,7Hz), 3.63 (3H,s), 2.26 & 2.10 (2H,m), 1.55 (4H,m) |
| Ig-70 | 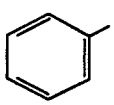 | 2 | A + B | 8.50 (2H,m), 7.30 (6H,m), 6.14 & 6.10 (1H,t,7Hz), 2.26 & 2.09 (2H,m), 1.55 (4H,m) |
| Ig-71 | 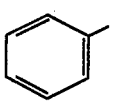 | 5 | A + B | 8.48 (2H,m), 7.31 (7H,m), 3.65 (3H,s), 6.16 & 6.07 (1H,t,7Hz), 2.28 (2H,t,7Hz), 2.11 (2H,m), 1.58 (2H,m), 1.30 (10H,m) |
| Ig-72 | 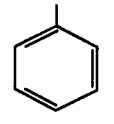 | 2 | E | 8.46 (2H,m), 7.44 (1H,d,5Hz), 7.32 (3H,m), 7.15 (3H,m), 6.09 (1H,t,7Hz), 3.66 (3H,s,Me), 2.26 (2H,t,7Hz), 2.13 (2H,t,7Hz), 1.55 (4H,m) |
| Ig-73 | 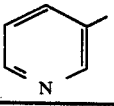 | 2 | Z | 8.50 (2H,m), 7.48 (1H,d,6Hz), 7.23 (6H,m), 6.16 (1H,t,7Hz), 3.66 (3H,s), 2.27 (2H,t, 7Hz), 2.09 (2H,t,7Hz), 1.56 (4H,m) |
| Ig-74 |  | 2 | — | 8.60 (1H,m), 8.48 (3H,m), 7.45 (4H,m), 6.21 (1H,t,7Hz), 3.64 (3H,s), 2.28 (2H,m), 2.21 (2H,m), 1.57 (4H,m) |

*1, *2 Refer to Table 3-1 and 3-2

TABLE 6

$$C=CHCH_2Y(CH_2)_nCOOR^3 \quad \text{(Ii)}$$

(with phenyl and pyridyl substituents on the C=C)

| Compound No. | Y | n | Isomer[*1, *2] R³ (m.p.) | NMR Spectrum (value, p.p.m., TMS internal standard) |
|---|---|---|---|---|
| Ii-75 | $CH_2$ | 2 | E, H (163–165° C.) | 10.40 (1H,COOH), 8.75 (1H,d,5Hz), 8.61 (1H,d,2Hz), 8.23 (1H,d,8Hz), 7.91 (1H,d, d,8 & 5Hz), 7.40 (3H,m), 7.18 (2H,m), 6.52 (1H,t,7Hz), 2.14 (4H,m), 1.48 (4H,m) |
| Ii-76 | $CH_2$ | 2 | E, Na | 8.35 (2H,m), 7.33 (7H,m), 6.15 (1H,t,7Hz), 1.99 (4H,m), 1.40 (4H,m) |
| Ii-77 | (2-methyl-4-methoxyphenyl acetate) | 0 | A, H | 8.57 (1H,m), 8.40 (1H,m), 6.80–7.80 (10H,m), 6.42 (1H), 4.65 (2H), 2.26 (3H) |
| Ii-78 | (3-methyl-4-methoxyphenyl acetate) | 0 | A, H | 9.60 (2H), 8.57 (1H), 8.40 (1H), 6.90–7.65 (10H), 4.50 (2H), 6.37 (1H), 2.25 (3H) |

[*1, *2] Refer to Table 3-1 and 3-2

EXPERIMENT 1

Inhibitory Action on Thromboxane $A_2(TXA_2)$ Synthetase

As a specimen of $TXA_2$ synthetase was employed horse platelet microsomes treated with indomethacin (indomethacin-treated horse platelet microsomes: IPM), which were prepared according to the method described by Needleman et al. (Science 193 163, 1967).

To 60 μl of 50 mM tris-buffer solution (pH 7.5) of IPM (containing 140 μg as protein) was added 60 μl of the buffer solution or the solution containing the test compounds at various concentrations. The mixtures were left standing for 5 minutes at room temperature. Then at 0° C. to 100 μl portion of the mixture was added 20 μl of the buffer solution containing 30 ng of prostanglandin $H_2(PGH_2)$. The mixtures were left standing for 5 minutes at 0° C. to cause formation of thromboxane $A_2(TXA_2)$. The reaction of thromboxane $A_2$ production was stopped by the addition of 500 μl of the tris-buffer to the mixture. Using 50 μl of the mixtures, the quantitative determination of thromboxane $B_2(TXB_2)$, a stable metabolite of $TXA_2$, was done by means of the radioimmunoassay (Shibouta et al., Biochem. Pharmacol. 28 3601, 1979). The inhibitory activity of the compounds on $TXA_2$-synthetase was determined from the difference in the production of $TXB_2$ between the test group and the control group.

The results on typical compounds are shown by Table 7 below:

TABLE 7

Inhibitory Action on Thromboxane $A_2$ Synthetase

| | % Inhibition on thromboxane $A_2$ synthetase | |
|---|---|---|
| Compound No. | Concentration of $3 \times 10^{-8}$ M | Concentration of $10^7$ M |
| Ia-4 | 58.5 | 92.8 |
| Ia-6 | 64.3 | 98.6 |
| Ia-8 | 55.7 | 93.3 |
| Ia-10 | 36.2 | 90.4 |
| Ib-13 | 78.5 | 95.7 |
| Ib-16 | 49.1 | 89.0 |
| Ib-20 | 82.5 | 96.6 |
| Ib-21 | 50.1 | 94.1 |
| Ib-22 | 75.8 | 98.3 |
| Ib-30 | 30.6 | 84.6 |
| Ig-66 | 19.4 | 65.9 |
| Ii-75 | 56.2 | 92.3 |

EXAMPLE 8

Promoting Action of Prostaglandin $H_2$(PGH$_2$) or Prostaglandin $G_2$(PGG$_2$) on Bio-synthesis of Blood-wall Prostaglandin $I_2$(PGI$_2$)

Blood platelet aggregation experiment was performed according to the method described by Born (Nature 194, 927 1962).

To 250 μl of the rabbit platelet-rich plasma prepared by a conventional method was added 25 μl of 50 mM tris-buffer solution (pH 7.5) containing a test compound in a given concentration. The mixture was stirred for 2 minutes. To this mixture was added 1 mg of a strip of the aorta (containing PGI$_2$-synthesizing enzyme activity) of the rat. Two minutes later, 25 μl (0.21 mM) of arachidonic acid was added to determine blood platelet aggregation ability.

Six minutes after the addition of arachidonic acid, 20 μl each portion was taken from each sample solution, and thromboxane B$_2$(TXB$_2$: a stable metabolite of TXA$_2$) and 6-Ketoprostaglandin F$_{1\alpha}$ (6-Keto-PGF$_{1\alpha}$) (a stable metabolite of PGI$_2$) were determined by the radioimmunoassay (Shibouta et al. Biochem. Pharmacol. 28 3601, 1979) and (Terashita et al., Japan, J. Pharmacol., 32, 351, 1982). Blood platelet aggregation ability and the respective amounts of TXB$_2$ and 6-Keto-PGF$_{1\alpha}$ produced were compared in the respective cases where the rat aortic strip was added or not.

In Table 8, when the aortic strip was not added, the ratio of blood platelet aggregation in response arachidonic-acid (0.21 mM) stimulation was 100%, and, at this time, 32 ng of TXB$_2$ was produced and no 6-Keto-PGF$_{1\alpha}$ was observed. When $10^{-6}$M of 7-phenyl-7-(3-pyridyl)-6-heptenoic acid (Ia-4) was allowed to act, the aggregation ratio was 93%, slightly suppressed. In this case, the production of TXB$_2$ was almost completely suppressed (2 ng). When the aortic strip was added, the aggregation ratio was suppressed to 70% and the amount of TXB$_2$ decreased from 32 ng to 27 ng while the amount of 6-Keto-PGF$_{1\alpha}$ increased from 0 to 22 ng. In contrast to the above, when the aortic strip and $10^{-6}$M of (Ia-4) were allowed to coexist, the aggregation ratio was further suppressed to 31%, while the amount of 6-Keto-PGF$_{1\alpha}$ remarkably increased from 22 ng up to 38 ng.

From these results, the compound (Ia-4) is considered to be able of completely suppress the biosynthesis of TXA$_2$ from arachidonic acid in blood platelet, and, when an aortic strip coexists, it is able to accelerate the utilization of PGH$_2$ and PGG$_2$, precursors of TXA$_2$, to the synthesis of PGI$_2$ in the blood vessel.

TABLE 8

Effects of the compound (Ia-4) and the aortic strip on rabbit blood platelet aggregation due to arachidonic acid and on production of TXB$_2$ and 6-Keto-PGF$_{1\alpha}$

| | Blood Platelet aggregation ratio (%) | TXB$_2$ ng | 6-Keto-PGF$_{1\alpha}$ ng |
|---|---|---|---|
| Addition of aortic strip | 100 | 32 | 0 |
| Non-addition of aortic strip + (Ia-4) $10^{-6}$ M | 93 | 2 | 0 |
| Addition of aortic strip | 70 | 27 | 22 |
| Addition of aortic strip + (Ia-4) $10^{-6}$ M | 31 | 1 | 38 | arachidonic acid 0.21 mM
aortic strip 1 mg

EXAMPLE 9

Sodium amide (31 g, 0.79 mole) was added to dimethyl sulfoxide (350 ml) under nitrogen and the mixture was stirred at room temperature for 10 minutes. 5-Carboxypentyltriphenylphosphonium bromide (140 g, 0.306 mole) was added with the temperature being maintained at 40° C. or lower, and the mixture was stirred for an hour. A solution of 3-benzoylpyridine (55 g, 0.301 mole) in dimethylsulfoxide (50 ml) was added dropwise to the above mixture with stirring at room temperature. After completion of addition, the reaction was allowed to proceed at room temperature for an additional 30 minutes. Water (700 ml) was added and the neutral substance was extracted twice with toluene. The aqueous layer was adjusted to pH 5.5 with 6N hydrochloric acid and extracted twice with ethyl acetate. The organic layer was washed with water, dried, and concentrated under reduced pressure to give an equimolar mixture (71.0 g) of (E)- and (Z)-7-phenyl-7-(3-pyridyl)-6-heptenoic acid. The mixture was dissolved in a mixture of 47% hydrobromic acid (300 ml) and water (300 ml), and the resulting mixture was heated at 110° C. for 18 hours. After cooling, the mixture was adjusted to pH 5.5 with 50% aqueous sodium hydroxide and extracted twice with ethyl acetate. The organic layer was washed with water, dried and concentrated under reduced pressure. The resulting oily product was dissolved in ethyl acetate (100 ml) and the solution was allowed to stand at room temperature for a day to give a crystalline product, which was collected by filtration to give (E)-7-phenyl-7-(3-pyridyl)-6-heptenoic acid (28.6 g, 33.8%).

Concentration of the filtrate gave a mixture (40.4 g) of (E)- and (Z)-7-phenyl-7-(3-pyridyl)-6-heptenoic acid (E form/Z from ratio=17:23). This mixture was repeatedly subjected to acid isomerization in the same manner as mentioned above to give a further crop (16.7 g, 19.7%) of (E)-7-phenyl-7-(3-pyridyl)-6-heptenoic acid.

Acid isomerization in the same manner as above was repeated twice to give (E)-7-phenyl-7-(3-pyridyl)-6-heptenoic acid (12.3 g, 14.5%).

The whole crystalline product (57.6 g) obtained by the above acid isomerization and crystallization procedure was crystallized twice from ethyl acetate (120 ml) to give (E)-7-phenyl-7-(3-pyridyl)-6-heptenoic acid (52.3 g, 61.7%) having a purity of not less than 99%. Mp 114°–115° C.

Elemental analysis: Calcd. for $C_{18}H_{19}NO_2$: C, 76.84; H, 6.81; N, 4.98, Found: C, 76.76; H, 6.69; N, 4.68.

Nuclear magnetic resonance spectrum [δ, p.p.m.; TMS internal standard: (the same in all examples that follows)]: 11.8 (1H, COOH), 8.55 (2H, m), 7.46 (1H, d, 7 Hz), 7.31 (3H, m), 7.16 (3H, m), 6.13 (1H, t, 7 Hz), 2.29 (2H, t, 7 Hz), 2.13 (2H, t, 7 Hz), 1.58 (4H, m).

EXAMPLE 10

Sodium hydride (1 g, 60% in oil) was added to dimethyl sulfoxide (25 ml) under nitrogen and the mixture was heated at 85° C. with stirring for an hour. The reaction mixture was cooled to room temperature and 5-carboxypentyltriphenylphosphonium bromide (5.2 g, 11 mmoles) was added gradually. The mixture was stirred for 10 minutes and a solution of 3-(3,4-methylenedioxybenzoyl)pyridine (2.5 g, 0.11 mole) in tetrahydrofuran (10 ml) was added dropwise thereto. After completion of addition, the mixture was further stirred at room temperature for 30 minutes. After completion of the reaction, water (100 ml was added and the neutral substance was extracted twice with toluene (50 ml). The aqueous layer was adjusted to pH 5.5 with 2N hydrochloric acid and extracted with ethyl acetate. The organic layer was washed with water, dried (magnesium sulfate) and concentrated under reduced pressure. The residue was subjected to silica gel column chromatography using ethyl acetate as the eluent. The eluate was concentrated and the residue was crystallized from ethyl acetate-isopropyl ether to give (Z)-7-(3,4-methylenedioxyphenyl)-7-(3-pyridyl)-6-heptenoic acid (0.4 g, 24.6%). Mp 90°–91° C.

Nuclear magnetic resonance spectrum: 9.20(COOH), 8.46 (2H, m), 7.50 (1H, m), 7.30 (1H, m), 6.68 (1H, d, 2 Hz), 6.68 (1H, d, 8 Hz), 6.53 (1H, dd, 8 Hz, 2 Hz), 6.05 (1H, t, 7 Hz), 5.92 (2H, s), 2.28 (2H, m), 2.03 (2H, m), 1.57 (4H, m).

The above-obtained (Z) isomer (0.3 g) was dissolved in 18% aqueous hydrochloric acid and the solution was heated at 110° C. for 20 hours. After completion of the reaction, the reaction mixture was adjusted to pH 5.5 with aqueous ammonia and extracted with ethyl acetate. High performance liquid chromatography of this product revealed that the E isomer/Z isomer ratio was E/Z=51:21. Liquid chromatography of this mixture (0.26 g) using Lobar LiChroprep RP-8 (40–63 um; E. Merck, Darmstadt) separated the mixture into the Z isomer, which was first eluted, and the E-isomer, which was later eluted. Concentration of the E-isomer fraction gave (E)-7-(3,4-methylenedioxyphenyl)-7-(3-pyridyl)-6-heptenoic acid (0.14 g).

Nuclear magnetic resonance spectrum: 10.30 (1H, COOH), 8.50 (2H, m), 7.47 (2H, m), 6.80 (1H, d, 8 Hz), 6.60 (1H, d.d., 8 Hz, 2 Hz), 6.57 (1H, d, 2 Hz), 6.06 (1H, t, 7 Hz), 5.96 (2H, s), 2.31 (2H, m), 2.16 (2H, m), 1.58 (4H, m).

EXAMPLE 11

Sodium hydride (60% in oil, 10 g, 0.25 mole) was added to dimethyl sulfoxide (250 ml) under argon and the mixture was stirred at 85° C. for an hour. The mixture was then cooled to room temperature and 5-carboxypentyltriphenylphosphonium bromide (52 g, 0.11 mole) was added gradually with the temperature being maintained at 40° C. The resulting mixture was stirred for 10 minutes, and a solution of 2-nicotinoylthiophene (20 g, 0.11 mole) in tetrahydrofuran (60 ml) was added dropwise. After the addition, the mixture was stirred at room temperature for 30 minutes, and water (300 ml) was added. The aqueous solution was extracted twice with toluene (300 ml) to remove the neutral substance. The aqueous layer was adjusted to pH 5.5 with 2N hydrochloric acid and extracted with ethyl acetate. The ethyl acetate layer was washed with water, dried (magnesium sulfate) and concentrated under reduced pressure. The residue was subjected to silica gel column chromatography using ethyl acetate as eluant and the eluate was concentrated. The resulting oily product was dissolved in ethyl acetate and the solution was allowed to stand overnight to give (Z)-7-(3-pyridyl)-7-(2-thienyl)-6-heptenoic acid (9 g, 29%). Mp 93°–94° C.

Nuclear magnetic resonance spectrum: 11.90 (1H, COOH), 8.53 (2H, m), 7.62 (1H, m), 7.20 (1H, m), 7.15 (1H, m), 6.85 (1H, m), 6.48 (1H, m), 6.22 (1H, t, 7 Hz), 2.35 (4H, m), 1.63 (4H, m).

The Z isomer (1.0 g) obtained in the above reaction was dissolved in 50% aqueous phosphoric acid (10 ml) and the solution was heated at 100° C. for 16 hours. After completion of the reaction, the reaction mixture was adjusted to pH 5.5 with aqueous ammonia, followed by extraction and separation in the conventional manner. High performance liquid chromatography of this crude product revealed that the E isomer/Z isomer ratio was E/Z=76:14. The crude product (0.92 g) was recrystallized from ethyl acetate to give (E)-7-(3-pyridyl)-7-(2-thienyl)-6-heptenoic acid (0.65 g). Mp. 84°–85° C.

Nuclear magnetic resonance spectrum: 10.50 (1H, COOH), 8.59 (1H, d, 2 Hz), 8.48 (1H, d.d, 2 Hz, 4 Hz), 7.58 (1H, d, t, 7 Hz, 2 Hz), 7.29 (1H, m), 7.24 (1H, d.d, 4 Hz, 7 Hz), 7.04 (1H, m), 6.85 (1H, m), 6.04 (1H, t, 8 Hz), 2.34 (4H, m), 1.64 (4H, m).

What is claimed is:

1. 7-Phenyl-7-(3-pyridyl)-6-heptenoic acid or a pharmaceutically acceptable salt thereof.

2. A method of inhibiting the activity of thromboxane synthetase in a mammal which comprises administering to said mammal an effective amount of 7-phenyl-7-(3-pyridyl)-6-heptenoic acid or a pharmaceutically acceptable salt thereof.

* * * * *